United States Patent
Zhao et al.

(10) Patent No.: US 10,364,446 B2
(45) Date of Patent: Jul. 30, 2019

(54) STREPTOMYCES PSAMMOTICUS AND METHODS OF USING THE SAME FOR VANILLIN PRODUCTION

(71) Applicant: XIAMEN OAMIC BIOTECHNOLOGY CO., LTD., Xiamen (CN)

(72) Inventors: Xijing Zhao, Xiamen (CN); Chenguang Xing, Xiamen (CN); Zhiqiang Huang, Xiamen (CN); Wei Liu, Xiamen (CN); Hongcan Gong, Xiamen (CN)

(73) Assignee: XIAMEN OAMIC BIOTECHNOLOGY CO., LTD., Xiamen (CN)

( * ) Notice: Subject to any disclaimer, the term of this patent is extended or adjusted under 35 U.S.C. 154(b) by 0 days.

(21) Appl. No.: 15/575,264

(22) PCT Filed: Jan. 13, 2016

(86) PCT No.: PCT/CN2016/070788
§ 371 (c)(1),
(2) Date: Nov. 17, 2017

(87) PCT Pub. No.: WO2017/016199
PCT Pub. Date: Feb. 2, 2017

(65) Prior Publication Data
US 2018/0142270 A1 May 24, 2018

(30) Foreign Application Priority Data
Jul. 27, 2015 (CN) .......................... 2015 1 0446456

(51) Int. Cl.
*C12P 7/24* (2006.01)
*C12N 1/20* (2006.01)
*C12R 1/465* (2006.01)

(52) U.S. Cl.
CPC .............. *C12P 7/24* (2013.01); *C12N 1/20* (2013.01); *C12R 1/465* (2013.01)

(58) Field of Classification Search
None
See application file for complete search history.

(56) References Cited

U.S. PATENT DOCUMENTS

2009/0186399 A1* 7/2009 Xu ........................... C12P 7/24
435/253.5

FOREIGN PATENT DOCUMENTS

| CN | 1421523 A | 6/2003 |
| CN | 101165168 A | 4/2008 |
| CN | 105132472 A | 12/2015 |
| EP | 2157184 A1 | 2/2010 |
| EP | 0885968 B3 | 10/2012 |

OTHER PUBLICATIONS

Kim et al. J Agric Food Chem. Mar. 9, 2011;59(5):1893-9 (Year: 2011).*
Sarang et al. Asian Journal of Microbiology, Biotechnology & Environmental Sciences (2009), 11(2), 273-278 (Abstract) (Year: 2009).*
Peela et al. Journal of Pharmacy Research (2012), 5(8), 4480-4483 (Abstract) (Year: 2012).*

* cited by examiner

*Primary Examiner* — Christian L Fronda
(74) *Attorney, Agent, or Firm* — Rabin & Berdo, P.C.

(57) ABSTRACT

The present invention relates to a bacterial strain, *Streptomyces psammoticus* OMK-4, and a method for vanillin production by fermentation of the bacterial strain. The method of the fermentation includes the following steps: activating the strain, culturing the seed, fermenting, extracting and so on. This method using ferulic acid as one of the raw materials to produce vanillin through microbial fermentation is safe and environmentally friendly.

4 Claims, 3 Drawing Sheets

STREPTOMYCES PSAMMOTICUS AND METHODS OF USING THE SAME FOR VANILLIN PRODUCTION

BACKGROUND OF THE INVENTION

This invention relates to the use of *Streptomyces psammoticus* and the method for producing vanillin.

BACKGROUND OF THE INVENTION

Vanillin is also referred to as vanilla aldehyde. The molecular weight of vanillin is 152.14. The common form of vanillin is crystal with white to light yellow color. Vanillin has the melting point of 81° C. and the boiling point of vanillin ranges from 284° C. to 285° C. The specific gravity of vanillin is 1.060.

The flash point of vanillin is 147° C. and the solubility of vanillin is 10 g/L (25° C.) Vanillin is soluble in ethanol and other organic solvents. Vanillin can be found in Peruvian balsam, tallow, vanilla, coffee, grape and brandy. Vanillin smells like vanilla and sweet.

Vanillin is not only an important spice but also an important chemical raw material and an important pharmaceutical intermediate. In the food field, because Vanillin has the aroma of vanilla bean, Vanillin is used as a fixative in various kinds of food. In medicine, vanillin is the raw material for synthesizing medicine intermediates. Vanillin is used to produce drugs commonly used for treating high blood pressure, heart diseases and skin diseases.

1. Chemical Synthesis

1) Lignin method: lignin is widely found in wood and pulp waste. Using lignin as raw material by hydrolysis and oxidation in alkaline medium and so on, vanillin is obtained. Although via the lignin method the cost of the raw materials is low, the yield and quality of vanillin is also low. The lignin method produces vanillin that generally is not used in the food and pharmaceutical industry.

2) Eugenol method: eugenol is the main component of clove oil. In the eugenol method, eugenol is oxidized to obtain the vanillin.

3) Guaiacol method: there are several routes for producing vanillin by guaiacol synthesis. The highest yield of vanillin via guaiacol method reaches 60%. The yield of vanillin by the guaiacol method is usually less than 60%. The guaiacol method is the main production method of vanillin in China.

4) P-hydroxy benzaldehyde, nitrotoluene and p-cresol method: for various reasons, these three methods have not yet been industrialized. The p-hydroxy benzaldehyde method is due to the high price of raw materials. The p-cresol method has strict reaction conditions and low yield. The nitrotoluene method needs large equipment.

5) Safrole method: Safrole is mainly extracted from the camphor oil. The safrole method has long reaction route. The by-products from the safrole method are difficult to separate.

2. Plant Extraction

In the plant extraction, vanillin is mainly extracted vanillin from vanilla beans, but due to the planting of the vanilla beans is restricted by geographical conditions and the vanillin content in the vanilla beans is low, the vanillin extracted from the vanilla beans had low yield and dose not meet the demand of the market. Vanillin produced via the plant extraction is difficult to be accepted by average consumers because of the high price.

3. Biological Transformation Method

The biological transformation method mainly includes plant cell culture method and microorganism transformation method. The cultivation of plant cell culture has relatively long culture period and low yield. The plant cell culture method is not beneficial for industrialization. There are a variety of microorganisms capable of transforming anacylic acid or iso-eugenol to vanillin. The microorganism transformation method takes advantage of short producing period, high yield and low pollution. The microorganism transformation method is beneficial to industrial production.

4. Enzymatic

It has now been found that the eugenol or isoeugenol can be converted into vanillin by the catalysis of lipid oxygenase. The catalytic reaction of lipid oxygenase is mild and the product of lipid oxygenase is easy to purify. However the separation, directed evolution and modification of lipid oxygenase need further study, and the enzymatic method is still in research phase.

In conclusion the aforementioned methods all have some kind of shortcomings.

SUMMARY OF THE INVENTION

The purpose of this invention is to provide the use of *Streptomyces psammoticus* and the method for producing vanillin by *Streptomyces psammoticus*, in order to solve the existing problems in the current microbial transformation technology.

The objects of the invention are achieved by providing:

The use of *Streptomyces psammoticus* OMK-4, which is used for the production of vanillin.

The method for producing vanillin wherein the production of vanillin is by the use of *Streptomyces psammoticus* OMK-4.

The method for producing vanillin wherein the said method is by the fermentation of *Streptomyces psammoticus* OMK-4.

The method for producing vanillin comprises the following steps:

1) under aseptic conditions, a full inoculation loop of bacteria from the glycerol stock tube is spread evenly over the solid agar slant wherein the said bacteria is *Streptomyces psammoticus* OMK-4. The agar slants containing *Streptomyces psammoticus* OMK-4 are then cultured in a biochemical incubator at 26-30° C. for 24-48 hours. The solid agar slants by weight percentage comprise the following components: soluble starch 1.0-3.5%, $KH_2PO_4$ 0.1-1.0%, NaCl 0.05-0.3% and yeast extract powder 0.1-1.0%.

2) seed culture: under aseptic conditions, a full inoculation loop of the well-grown cells from the ager slant is inoculated into the seed culture medium. The initial pH value of the seed culture medium is 5-8. Under the conditions of 28-35° C. culture temperature and 200-500 rpm shaking speed, cells are cultured until exponential growth phases.

by weight percentage the said seed culture medium comprises the following components: soluble starch 1.0-3.5%, $KH_2PO_4$ 0.1-0.5%, urea 0.1-0.3%, $MgSO_4$ 0.05-0.1%, $CaCO_3$ 0.1-0.3%, yeast extract powder 0.1-1.0%, corn syrup 0.1-1.0%, $(NH_4)_2SO_4$ 0.1-0.6% and ferulic acid 0.1-0.3%.

3) fermentation: the cells in exponential growth phase are inoculated into a fermentation medium with the volume ratio of 5-15% under aseptic conditions. The initial pH of the fermentation medium is 7.2 to 7.8. Under the conditions of 30-40° C. temperature, 200-500 rpm shaking speed and 1:0.5 ventilation, the cells are fermented for 70-120 hours.

The fermentation medium by weight percentage comprises the following components: soluble starch 2.0-5.0%, $KH_2PO_4$ 0.1-0.3%, urea 0.1-0.5%, $MgSO_4$ 0.05-0.1%, $CaCO_3$ 0.5-2.0%, yeast extract powder, 0.1-1.0%, $(NH_4)_2SO_4$ 0.1-0.5% and ferulic acid 0.1-3.0%.

4) extraction: extract the vanillin from the fermentation medium. After the completion of the fermentation process, the fermentation medium is pasteurized at 80° C. and filtrated by ceramic membrane to remove bacteria and large molecular weight proteins; Then small molecular weight proteins and pigments are further filtrated out by ultrafiltration. The ultrafiltrate is RO treated for 5 to 10 times to concentrate the vanillin crude product. The vanillin crude product is obtain by adjusting the pH of the concentrated liquid to 5-6 and is allowed to cool for crystallization.

*Streptomyces psammoticus* OMK-4 of the invention has been preserved at the China Center for Type Culture Collection, Wuhan University, Wuhan, Hubei Province on May 27, 2015, with the preservation number of CCTCC M 2015329.

For the first time, the applicant finds that the strain of the *Streptomyces* bacteria has the ability to produce vanillin and utilize the ability of the *Streptomyces* bacteria to the production of vanillin.

The method of the invention uses ferulic acid as one of the raw materials to produce vanillin through microbial fermentation at low-temperature and low-pressure. The said method is a safe and easy to operate method. The said method produces less pollution and is environmentally-friendly.

PREFERRED EMBODIMENTS OF THE INVENTION

1, The Strain

Figure 1A:
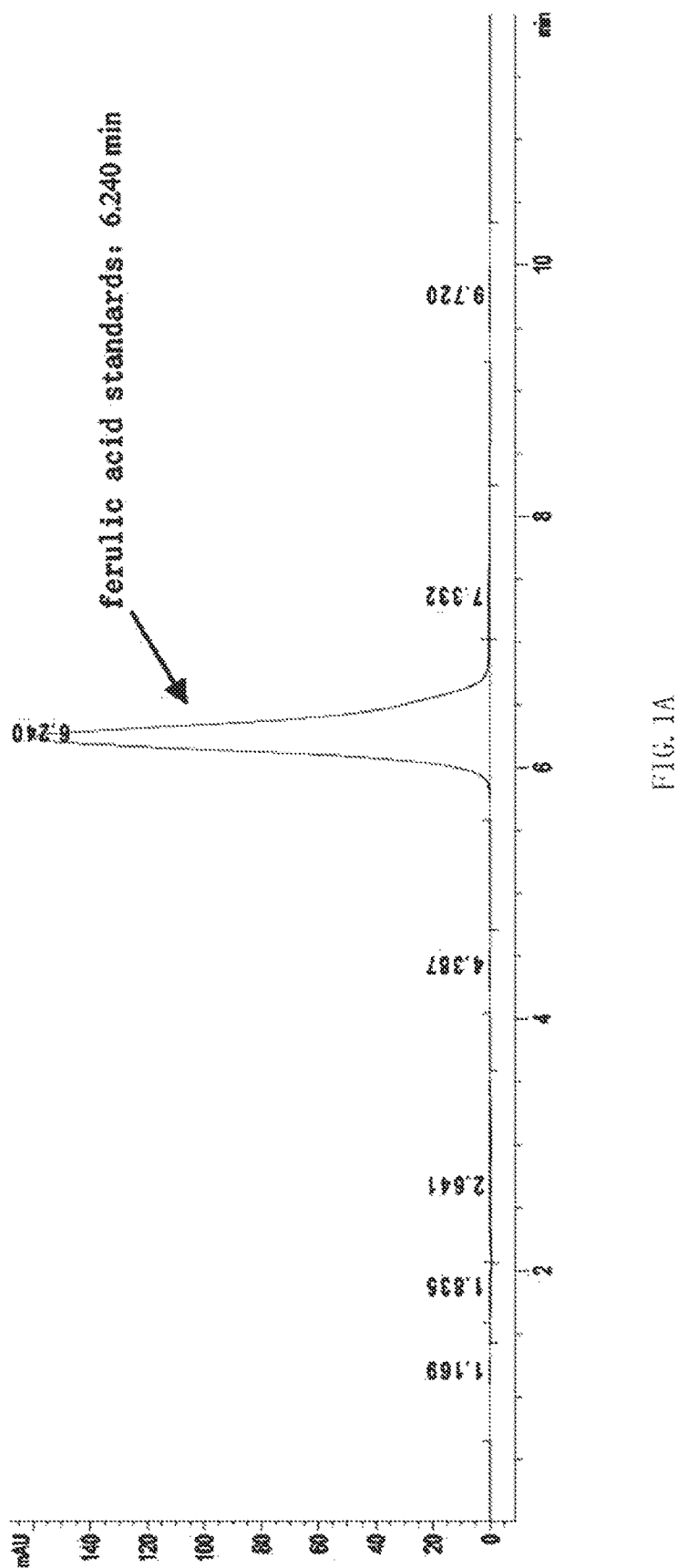
FIG. 1A HPLC diagram of ferulic acid standards.

The *Streptomyces psammoticus* OMK-4 capable of producing natural vanillin was isolated from the soil of a cinnamon plantation forest. The said strain has been preserved at the China Center for Type Culture Collection, Wuhan University, Wuhan, Hubei Province on May 27, 2015, with the preservation number of CCTCC M 2015329.

*Streptomyces psammoticus* OMK-4 is a gram-positive bacterium. *Streptomyces psammoticus* OMK-4 grows less well in cica culture. *Streptomyces psammoticus* OMK-4 has straight spore chain when observed under the light microscope. The spores of *Streptomyces psammoticus* OMK-4 are phalange shape. *Streptomyces psammoticus* OMK-4 is able to use glycogen and dextrin as energy sources, but *Streptomyces psammoticus* OMK-4 is not able to use carbon sources such as d-fructose, d-fiber diose, etc. as energy sources. The results of the 16S rRNA gene of *Streptomyces psammoticus* OMK-4 were identical to that of *Streptomyces psammoticus*, so it was identified as a strain of *Streptomyces psammoticus*.

1) Strain Activation

Under aseptic conditions, a full inoculation loop of bacteria from the glycerol stock tube is spread evenly over an agar slant wherein the said bacteria are *Streptomyces psammoticus* OMK-4. The agar slant containing *Streptomyces psammoticus* OMK-4 is cultured in a biochemical incubator at 28-30° C. for 24 to 48 hours.

By the percentage of weight, the agar slant comprises the following components: soluble starch 1.0-3.5%, $KH_2PO_4$ 0.1-1.0%, NaCl 0.05-0.3% and yeast extract powder 0.1-1.0%.

2) Seed Culture:

Under aseptic conditions, *Streptomyces psammoticus* OMK-4 that have grown well in the ager are inoculated into a sterile seed culture medium with a shovel. The initial pH of the seed culture medium is 5-8. Under the conditions of 28-35° C. cultivating temperature and 150-500 rpm shaking speed, *Streptomyces psammoticus* OMK-4 are cultured to the exponential growth phase.

By weight percentage the said seed culture medium comprises the following components: soluble starch 1.0-3.5%, $KH_2PO_4$ 0.1-0.5%, urea 0.1-0.3%, $MgSO_4$ 0.05-0.1%, $CaCO_3$ 0.1-0.3%, yeast extract powder 0.1-1.0%, corn syrup 0.1-1.0%, $(NH_4)_2SO_4$ 0.1-0.6% and ferulic acid 0.1-0.3%;

3) Fermentation:

*Streptomyces psammoticus* OMK-4 that have been cultured to exponential growth phase in the seed culture medium are added to a fermentation medium with the ratio of 10% V/V in aseptic conditions. The initial pH of the fermentation medium is 7.5. Under conditions of 30-40° C. culture temperature, 200-500 rpm shaking speed and 1:0.5 ventilation, *Streptomyces psammoticus* OMK-4 are fermented for 70-120 hours. The fermentation medium by weight percentage comprises the following components: soluble starch 2.0-5.0%, $KH_2PO_4$ 0.1-0.3%, urea 0.1-0.5%, $MgSO_4$ 0.05-0.1%, $CaCO_3$ 0.5-2.0%, yeast extract powder 0.1-1.0%, $(NH4)_2SO_4$ 0.1-0.5% and ferulic acid 0.1-3.0%.

Embodiment 1: The Production of Natural Vanillin (Flask Shaking Fermentation)

Preparation of the seed medium: the seed medium composition was as follow (g/L): glucose 20, $KH_2PO_4$ 3, urea 5, $MgSO_4$ 0.3, NaCl 1.0, yeast extraction powder 5, corn starch 5, $(NH_4)_2SO_4$ 6 and $CaCO_3$ 0.2. Water was used as solvent. The initial pH was 7.2. The seed culture medium was sterilized for 20 minutes at 121° C.

Preparation of the fermentation medium: the medium composition was as follow (g/L): glucose 30, $KH_2PO_4$ 5, urea 5, $MgSO_4$ 0.6, yeast extraction powder 8, $(NH_4)_2SO_4$ 3, $CaCO_3$ 1.0 and ferulic acid 20. Water was used as solvent. The initial pH was 7.2. The fermentation medium was sterilized for 20 minutes at 121° C.

Seed preparation: under aseptic conditions, the strain of *Streptomyces psammoticus* OMK-4 in low temperature glycerol tube was transferred into a fresh sterile medium plate for activation at 30° C. for 2 days. *Streptomyces psammoticus* OMK-4 colonies were inoculated into a 500 mL flask for seed culture. The volume of the seed culture medium was 50 mL. The flask containing *Streptomyces psammoticus* OMK-4 and the seed culture medium was incubated at 30° C. with the rotation speed of 180 rpm. Seed liquid was obtained after 16-24 hours of growth at the aforementioned conditions.

Natural vanillin fermentation: 50 mL of the prepared fermentation medium was introduced into a 500 mL sterile triangle flask, after which 7.5 mL of cultured seed liquid was inoculated into the fermentation medium for fermentation. The flask containing the seed culture and the fermentation medium was incubated at 37° C. with 200 rpm shaking speed. After being fermented for 80 hours, the concentration of natural vanillin in the fermentation medium was measured by HPLC method. The final concentration of natural vanillin in the fermentation medium was 10 g/L.

Embodiment 2: Natural Vanillin Production (Stirring Reactor Fermentation)

Seed medium and fermentation medium were prepared in the same way as described in embodiment 1.

Seed preparation: under aseptic conditions, the strain of *Streptomyces psammoticus* OMK-4 in low temperature glycerol stock tube was transferred into a fresh sterile medium plate for activation at 30° C. for 2 days. *Streptomyces psammoticus* OMK-4 colonies were inoculated into a 3 L tank equipped with 1.8 L seed medium. The tank containing *Streptomyces psammoticus* OMK-4 and 1.8 L seed medium was incubated with ventilation at 30° C. and 300 rpm stirring speed. Seed liquid was obtained after 13-18 hours of culture.

Figure 1B:
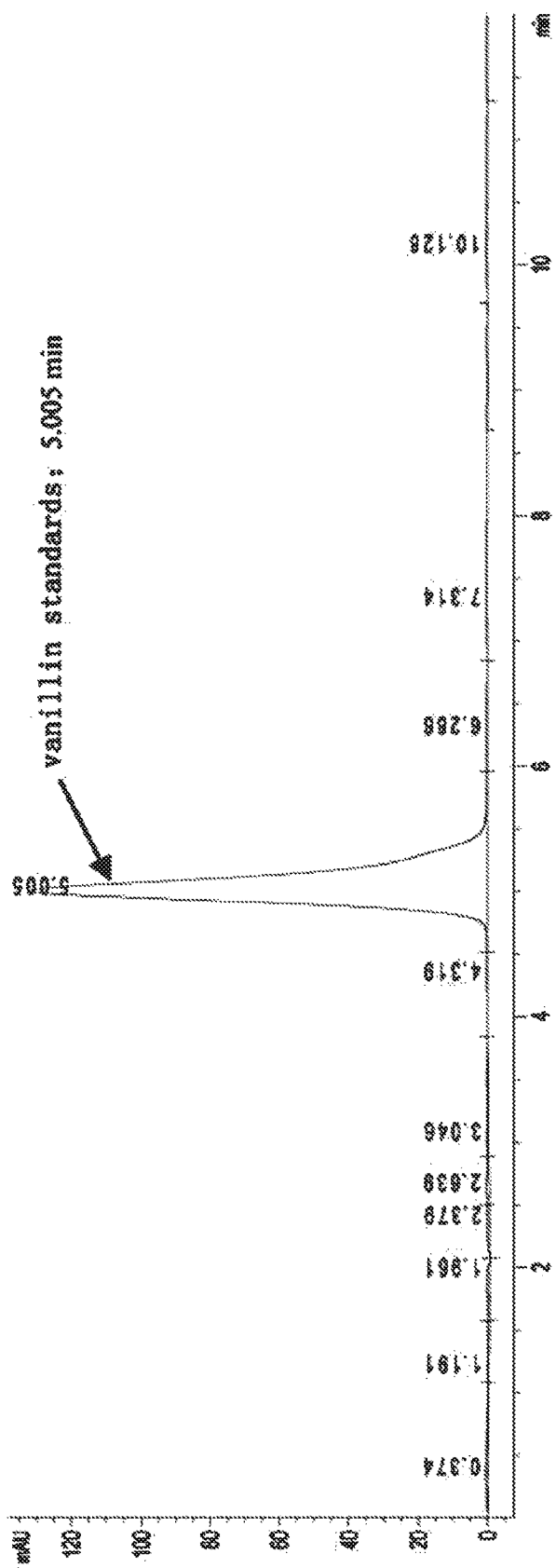
FIG. 1B HPLC diagram of vanillin standards.
Figure 1C:
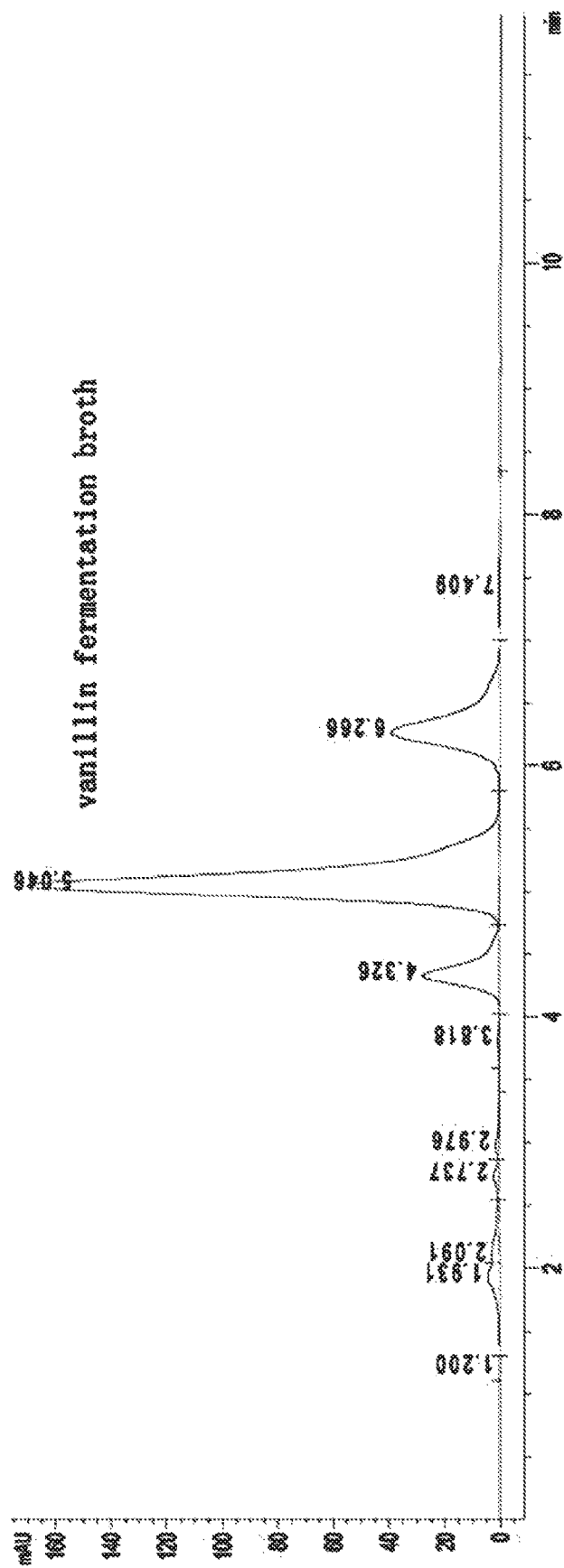
FIG. 1C HPLC diagram of vanillin fermentation broth
The Figures shows that the resulting product is vanillin.

The fermentation of natural vanillin: 10.2 L of the prepared fermentation medium was added into a 20 L fermentor. The fermentor with the fermentation medium was sterilized at 121° C. for 20 min, after which 1.8 L of cultured seed liquid was added into the 20 L fermentor for fermentation, with fermentation temperature of 37° C., stirring speed of 400 rpm and ventilation ratio of 1:0.2. The fermentation period was 90 hours. At the end of the fermentation, the concentration of natural vanillin in fermentation medium measured by HPLC method was 15 g/L. (shown in FIG. 1A to FIG. 1C)

Embodiment 3: The Extraction of Natural Vanillin

Twelve liters of the fermented medium of embodiment 2 which contained 15 g/L vanillin were filtrated by ceramic membrane at 80° C. Ten liters of filtrate were obtained, which was further treated by ultrafiltration (UF). The ultrafiltrate was further treated with reverse osmosis (RO). At the end 5 L of concentrate was obtained. The concentrate was adjusted to pH 5-6 and was allowed to cool for crystallization between 0° C. to 4° C. The concentrate was stranded for 4 hours. Raw natural vanillin was obtained from the concentrate by suction filter. One hundred and forty four gram of crude vanillin was obtained after drying. The purity of the crude vanillin was 98%.

INDUSTRIAL APPLICABILITY

The method of the invention is by fermentation at low temperature and low pressure. The merits of the process are that it is relatively safe with less environmental pollution and that the operation is simple.

What is claimed is:

1. A method for producing vanillin using *Streptomyces psammoticus* strain OMK-4 having preservation number CCTCC M 2015329, wherein the method comprises the steps of:
    1) strain activation;
    2) seed culture; and
    3) fermentation of ferulic acid to produce vanillin wherein strain activation step 1 comprises:
   under aseptic conditions, a full inoculation loop of strain OMK-4 from a glycerin stock tube is spread evenly over an agar slant and cultured in a biochemical incubator at 26-30° C. for 24-48 hours, and wherein by percentage of weight, the agar slant comprises the following components:
   soluble starch 1.0-3.5%, $KH_2PO_4$ 0.1-1.0%, NaCl 0.05-0.3% and yeast extract powder 0.1-1.0%, and wherein seed culture step 2 comprises:
   under aseptic conditions, a full inoculation loop of well-grown OMK-4 cells from the ager slant in step 1 is inoculated into a seed culture medium having an initial pH value of 5-8 and cultured at 28-35° C. with 200-500 rpm shaking until exponential growth phase, wherein the said seed culture medium by weight percentage comprises the following components:
   soluble starch 1.0-3.5%, $KH_2PO_4$ 0.1-0.5%, urea 0.1-0.3%, $MgSO_4$ 0.05-0.1%, $CaCO_3$ 0.1-0.3%, yeast extract powder 0.1-1.0%, corn syrup 0.1-1.0%, $(NH_4)_2SO_4$ 0.1-0.6% and ferulic acid 0.1-0.3%, and wherein fermentation step 3 comprises:
   the OMK-4 cells from step 2 in exponential growth phase are inoculated into a fermentation medium with the volume ratio of 5-15% under aseptic conditions wherein the initial pH of the fermentation medium is 7.2 to 7.8 at 30-40° C. and 200-500 rpm shaking and 1:0.5 ventilation, to ferment the cells for 70-120 hours, wherein the fermentation medium by weight percentage comprises the following components:
   soluble starch 2.0-5.0%, $KH_2PO_4$ 0.1-0.3%, urea 0.1-0.5%, $MgSO_4$ 0.05-0.1%, $CaCO_3$ 0.5-2.0%, yeast extract powder 0.1-1.0%, $(NH_4)_2SO_4$ 0.1-0.5% and ferulic acid 0.1-3.0%.

2. The method for producing vanillin according to claim 1, further comprising the steps of:
    4) extracting the vanillin produced by fermentation at step 3 by pasteurizing the fermentation liquid at 80° C., filtration through a ceramic membrane followed by ultrafiltration and treatment of the ultrafiltrate by reverse osmosis (RO) for 5 to 10 times to concentrate the vanillin crude product, and crystallizing the vanillin crude product by adjusting the pH of the concentrated liquid to pH 5-6 and cooling.

3. The method for producing vanillin according to claim 2, wherein filtration through a ceramic membrane in step 4 is to remove the OMK-4 cells and large molecular weight proteins.

4. The method for producing vanillin according to claim 2, wherein the ultrafiltration in step 4 is to remove small molecular weight proteins and pigments.

* * * * *